United States Patent [19]

Thiem et al.

[11] Patent Number: 4,749,785

[45] Date of Patent: Jun. 7, 1988

[54] PROCESS FOR THE PREPARATION OF GLYCOSIDES FROM GLYCOSYL FLUORIDES

[75] Inventors: Joachim Thiem, Münster; Wolfram Fritsche-Lang, Heppenheim; Merten Schlingmann, Königstein; Hans-Matthias Deger, Hofheim am Taunus; Matthias Kreuzer, Münster, all of Fed. Rep. of Germany

[73] Assignee: Hoechst Aktiengesellschaft, Fed. Rep. of Germany

[21] Appl. No.: 754,265

[22] Filed: Jul. 12, 1985

[30] Foreign Application Priority Data

Jul. 14, 1984 [DE] Fed. Rep. of Germany ....... 3426074

[51] Int. Cl.$^4$ ............................................. C07H 17/04
[52] U.S. Cl. .................................................... 536/18.6
[58] Field of Search ........................................ 536/18.6

[56] References Cited

FOREIGN PATENT DOCUMENTS 60-156699 8/1985 Japan .................................. 536/18.6

OTHER PUBLICATIONS

S. Hashimoto, M. Hayashi and R. Noyori, Tetrahedron Letters 25 (1984), 1379–1382.
K. M. Yamada and K. Olden, Nature 275 (1979), 179–1984.
R. Neumeier, Biol. in Unserer Zeit 13 (1983), 33–38.
Nicolau et al.; Journal of the American Chemical Society, No. 106; 1984; pp. 4189–4192.
Nicolau et al.; Journal of the Chemical Society Chemical Communication; 1984; pp. 1155 to 1156.

*Primary Examiner*—Ronald W. Griffin
*Attorney, Agent, or Firm*—Finnegan, Henderson, Farabow, Garrett and Dunner

[57] ABSTRACT

A process for the manufacture of glycosides which comprises reacting a protected hexopyranosyl fluoride with an aglycon or a silyl ether thereof in the presence of a metal fluoride of group IV or V of the periodic table, said metal having an atomic number of at least 22 and being present in the fluoride in a higher, stable and non-oxidizing or weekly oxidizing stage.

20 Claims, No Drawings

PROCESS FOR THE PREPARATION OF GLYCOSIDES FROM GLYCOSYL FLUORIDES

It is known that glucopyranosyl fluorides can be glycosided with trimethylsilyl ethers and also with unprotected alcohols, if silicon tetrafluoride or trimethylsilyl trifluoromethanesulfonate (TMSOTF) are employed as the catalyst. The reaction medium used is on the one hand acetonitrile, which leads mainly to the $\beta$-glycosides, and on the other hand diethyl ether, which leads mainly to the $\alpha$-anomer (S. Hashimoto, M. Hayashi and R. Noyori, Tetrahedron Letters 25 (1984) 1379–1382).

Of the two catalysts employed TMSOTF is admittedly cheaper and easier to handle, but is less effective than silicon tetrafluoride, which is a highly corrosive and aggressive gas. Working up is troublesome when either catalyst is used, but especially so with TMSOTF, since there the formation of trifluoromethanesulfonic acid must under all circumstances be avoided.

We have now found that in place of silicon tetrafluoride, which is a gas, fluorides of metals of the fourth and fifth group of the periodic table, which have an atomic number of not less than 22, in their higher, stable and non-oxidizing or slightly oxidizing oxidation states, can be used particularly advantageously for this glycosiding reaction. Examples of suitable metal fluorides, which also include transition metal fluorides, are tin tetrafluoride, zirconium tetrafluoride, vanadium pentafluoride, antimony pentafluoride and especially titanium tetrafluoride. The oily vanadium pentafluoride and antimonyepentafluoride are soluble in the reaction system and accordingly act in a homogeneous phase, while the other fluorides mentioned are solid and are insoluble or only sparingly soluble, which greatly facilitates their handling and isolation. Hence, reaction in a heterogeneous phase, especially with titanium tetrafluoride, is preferred.

The reaction is in general carried out in a solvent or inert medium customary for reactions of sugars, such as acetonitrile, diethyl ether, methylene chloride and/or nitrobenzene or mixtures of these with benzene, toluene or the like. In general, temperatures of $-40°$ to $+60°$ C., preferably of $-20°$ to $+30°$ C., are employed and reaction is carried out under atmospheric pressure, though superatmospheric pressure or reduced pressure can also be employed.

Depending on the reactivity and in particular on the steric arrangement of the groups in the reactants, the fluorides are employed in amounts of 1 to 200, preferably 10 to 120 and especially up to 100, mol % based on the glycosyl fluoride.

The glycosyl fluorides employed are protected hexopyranosyl fluorides, especially those derived from glucose, galactose and mannose. However, it is also possible to use derivatives of these sugars, such as 2-deoxy-2-amino-2-deoxy-glucose, -galactose and -mannose, as well as glucuronic, galacturonic and mannuronic acids and their derivatives, especially the esters, amides and nitriles. Suitable protective groups are not only the benzyl protective group, employed in the known process, but also, according to the invention, acyl protective groups, preferably the acetyl group and the benzoyl group. The choice of protective group can—depending on the fluoride employed according to the invention and on any solvent which may be employed—influence the ratio of the stereoisomers formed.

According to the invention, the aglycones are employed unblocked or in the form of their silyl ethers, for example the triethyl, tripropyl, triisopropyl and tributyl ethers or of mixed ethers, such as the t-butyldimethylsilyl ether, but especially as the trimethylsilyl ether. The reactivity can vary depending on the nature of the alkyl group. Suitable aglycones are, for example, straight-chain and branched aliphatic monohydric primary, secondary and tertiary $C_1$–$C_{10}$-alcohols and monohydric cycloaliphatic $C_5$–$C_7$-alcohols, above all monosaccharides, though also disaccharides, especially of the glucose, galactose and mannose series, of which the hydroxyl groups which are not to be glycosided are blocked by suitable protective groups. Protective groups which can be used are, depending on the requirements, acetals or ketals, ether structures such as benzyl ethers or triphenylmethyl ethers, or acyl, aryloxy or alkoxycarbonyl groups. Further particularly interesting protective groups are epoxides (in the glycone or aglycone), which are stable under the conditions of the glycoside synthesis according to the invention and can easily be cleaved in a subsequent reaction step. Phenolic aglycones as well as complex steroid alcohols such as 5 $\alpha$-cholestan3 $\beta$-ol can also be successfully glycosided.

The products of the process are known per se and are useful as intermediates for a large number of syntheses. They are suitable for use as model substances in investigating the interaction of antigens with partial structures of cell membranes, and are for this reason of interest as immune-modulators (K. M. Yamada and K. Olden, Nature 275 (1978) 179–184, R. Neumeier, Biol. in unserer Zeit 13 (1983) 33–38).

The examples which follow illustrate the invention in more detail:

EXAMPLES (1) 200 mg (0.37 mmol) of 2,3,4,6-tetra-O-benzyl-$\beta$-D-glucopyranosyl fluoride and 123 mg (0.37 mmol) of 1,2;3,4-di-O-isopropylidene-6-O-(trimethylsilyl)-$\alpha$-D-galactopyranose were dissolved in 3 ml of anhydrous acetonitrile and 23 mg (0.19 mmol) of titanium(IV) fluoride were added at 0° C. After the mixture had been stirred for 2 hours at 0° C., the course of the reaction being checked by thin-layer chromatography with methylene chloride/diethyl ether (20:1 v/v) as the migrating agent, the solution was concentrated, the residue was taken up in chloroform and the solution was filtered through silica gel (2 g). After the solvent had been stripped off, a mixture of 6-O-(2,3,4,6-tetra-O-benzyl-$\alpha$- and -$\beta$-D-glucopyranosyl)-1,2;3,4-di-O-isopropylidene-$\alpha$-D-galactopyranose was obtained in an amount of 255 mg (88% yield).

According to $^1$H-NMR analysis the anomer ratio $\alpha$:$\beta$ was 13:87. The anomers were separated by column chromatography (silica gel, methylene chloride/diethyl ether 20:1 v/v).

$\alpha$-glycoside: $^1$H-NMR $\delta$=4.98 (1'-H, J(1',2')=3.8 Hz), 5.50 (1-H, J(1, 2)=5.0 Hz).

$[\alpha]_D^{20}$: $+11°$(c=0.87, CHCl$_3$).

$\beta$-glycoside: $^1$H-NMR $\delta$=4.45 (1'-H, J(1', 2')=7.8 Hz), 5.57 (1-H, J(1, 2)=5.0 Hz).

$[\alpha]_D^{20}$: $-32°$(c=0.87, CHCl$_3$).

(2) 113 mg (0.21 mmol) of 2,3,4,6-tetra-O-benzyl-$\beta$-D-glucopyranosyl fluoride and 36 mg of (0.21 mmol) of trimethylsilyl cyclohexyl ether were dissolved in 2 ml of anhydrous acetonitrile and 27 mg (0.21 mmol) of titanium(IV) fluoride were added at 0° C. After 12 hours at 0° C., the course of the reaction being checked by thin-layer chromatography, using petroleum ether-/ethyl acetate (4:1 v/v), the solution was concentrated, the residue was taken up in methylene chloride and the mixture was filtered through silica gel (2 g). After the solvent had been stripped off, a mixture of cyclohexyl-2,3,4,6-tetra-O-benzyl-α- and -β-D-glucopyranoside was obtained in an amount of 99 mg (76% yield). The anomer ratio α:β found after separation was 69:31.

The anomers were separated by column chromatography (silica gel, methylene chloride).

α-glycoside: $^1$H-NMR δ=4.94 (1-H, J(1, 2)=3.8 Hz).
$[α]_D^{20}$: +42.5°(c=0.14, CHCl$_3$).
β-glycoside: $^1$H-NMR δ=4.49 (1-H, J(1, 2)=7.8 Hz).
Melting point 104°–105° C.
$[α]_D^{20}$: +9°(c=0.73, CHCl$_3$).

(3A) 36.4 mg (0.067 mmol) of 2,3,4,6-tetra-O-benzyl-β-D-glucopyranosyl fluoride and 14.5 mg (0.067 mmol) of 1,6,2,3-di-anhydro-4-O-trimethylsilyl-β-D-mannopyranose were dissolved in 1 ml of anhydrous acetonitrile and 8.3 mg (0.067 mmol) of titanium(IV) fluoride were added at 0° C. After 2 hours at 22° C., the solution was filtered, the filter was concentrated, the residue was taken up in methylene chloride and this mixture was filtered through silica gel (2 g). After the solvent had been stripped off under reduced pressure, the residue was purified by column chromatography (silica gel, methylene chloride/diethyl ether 20:1 v/v). A mixture of 1,6;2,3-di-anhydro-4-O-(2,3,4,6-tetra-O-benzyl-α- and -β-D-glucopyranosyl)-β-D-mannopyranose was obtained in an amount of 45 mg (44% yield). According to 1H-NMR analysis, the anomer ratio α:β was 45:55.

(3B) 1.1 g (2.03 mmol) of 2,3,4,6-tetra-O-benzyl-β-D-glucopyranosyl fluoride and 293 mg (2.03 mmol) of 1,6;2,3-di-anhydro-β-D-mannopyranose were dissolved in 10 ml anhydrous acetonitrile and 126 mg (1.02 mmol) of titanium(IV) fluoride were added at 0° C. After 2 hours at 0the solution was filtered through 10 g of silica gel, the silica gel was rinsed with ethyl acetate and the combined solutions were concentrated. 1.24 g (92%) of a crude product were obtained, containing, in addition to traces of the starting compound, an anomer mixture in the ratio of α:β=45:55. The anomers were separated by column chromatography on silica gel, with methylene chloride/diethyl ether 20:1.

Yield: α-glycoside: 460 mg (34%).
β-glycoside: 540 mg (40%).

The glycosides prepared according to examples (3A) and (3B) have the following characteristics:

α-glycoside: $^1$H-NMR: α=5.62 (1-H, J(1, 2)=3.1 Hz) 4.87 (1'-H, J(1',2')=3.6 Hz).
Melting point: 131°–135° C.
$[α]_D^{20}$: +32.5°(c=0.63, CHCl$_3$).
β-glycoside: $^1$H-NMR: δ=5.74(1-H, J(1,2)=2.6 Hz) 4.56 (1'-H, J(1',2')=7.8 Hz).
Melting point: 143°–144° C.
$[α]_D^{20}$: −2.3°(c=0.985, CHCl$_3$).

(4) 80 mg (0.23 mmol) of 2,3,4,6-tetra-O-acetyl-β-D-glucopyranosyl fluoride and 79 mg (0.23 mmol) of 1,2,3,4-di-O-isopropylidene-6-O-(trimethylsilyl)-α-D-galactopyranose were dissolved in 2 ml of anhydrous acetonitrile and stirred with 16 mg (0.13 mmol) of titanium(IV) fluoride at room temperature. After 2 hours, the starting compounds could only be detected in traces by thin-layer chromatography (methylene chloride/ethyl acetate 4:1 v/v). The solution was concentrated, the residue was taken up in methylene chloride and this mixture was filtered through silica gel. According to $^1$H-NMR analysis, exclusively 6-O-(2,3,4,6-tetra-O-acetyl-β-D-glucopyranosyl)-1,2; 3,4-di-O-isopropylidene-α-D-galactopyranose was obtained and this was purified by column chromatography (silica gel, methylene chloride/ethyl acetate 4:1 v/v) or by recrystallization from diethyl ether/petroleum ether. Yield: 89 mg (66%).

β-glycoside: $^1$H-NMR: δ=4.61 (1'-H, J(1',2')=7.9 Hz), 5.48 (1-H, J(1,2)=4.8 Hz).
Melting point: 140°–142° C.
$[α]_D^{20}$: −53°(c=1.05, CHCl$_3$).

(5)–(7) The reactions described in examples 1, 3A and 4 were carried out in the presence of identical mole amounts of tin tetrafluoride instead of titanium tetrafluoride as the catalyst, at 22° C., with acetonitrile as the solvent.

| No. | Time (hours) | Yield (%) | α:β Ratio |
| --- | --- | --- | --- |
| 5 | 2 | 89 | 15.85 |
| 6 | 72 | 49 | 31.69 |
| 7 | 24 | 44 | 0.100 |

(8) 600 mg (1.78 mmol) of methyl (2,3,4-tri-O-acetyl-β-D-galactopyranosyl fluoride)-uronate and 490 mg (1.77 mmol) of 1,6-anhydro-2-azido-4-O-benzyl-β-D-glucopyranose were dissolved in 10 ml of anhydrous acetonitrile and 100 mg (0.81 mmol) of titanium(IV) fluoride and 1 g of a 3 Å molecular sieve in powder form were added at room temperature. After the solution had been stirred for 2 hours, it was filtered through 5 g of silica gel, the filtrate was then concentrated and the crude product (1.06 g) was purified by chromatography (silica gel, n-hexane/ethyl acetate 2:1 v/v). Yield of pure 3-O-[Methyl-(2,3,4-tri-O-acetylβ-D-galactopyranosyl)-uronate]-1,6-anhydro-2-azido-4-O-benzyl-β-D-glucopyranose: 710 mg (67%).

$^1$ H-NMR (CDCl$_3$): δ=5.19 (1-H), 4.49 (1'-H, J(1', 2')=7.9 Hz).
Melting point: 68° C.
$[α]_D^{20}$=49.6°(c=1.97, CDCl$_3$).

We claim:
1. A process for the manufacture of glycosides which comprises reacting a protected hexopyranosyl fluoride with an aglycon or a silyl ether thereof in the presence of a metal fluoride of group IV or V of the periodic table, said metal having an atomic number of at least 22 and being present in the fluoride in a higher, stable and non-oxidizing or weakly oxidizing stage.

2. A process as claimed in claim 1, wherein the fluoride is titanium tetrafluoride, zirconium tetrafluoride, stannic fluoride, vanadium pentafluoride or antimony pentafluoride.

3. A process as claimed in claim 1, wherein the reaction is carried out in a heterogenic phase with a solid fluoride which is not or only scarcely soluble in the reaction system.

4. A process as claimed in claim 1, wherein the fluoride is applied in an amount of from 1 to 200 mole-%, referred to the hexopyranosyl fluoride.

5. A process as claimed in claim 4, wherein the amount is in the range from 10 to 120 mole-%.

6. A process as claimed in claim 4, wherein the amount is in the range from 10 to 100 mole-%.

7. A process as claimed in claim 1, wherein the reaction is carried out in the presence of a solvent or an inert medium.

8. A process as claimed in claim 1, wherein the reaction is carried out at a temperature in the range from −40° to +60° C.

9. A process as claimed in claim 1, wherein the reaction is carried out at a temperature in the range from −20° to +30 ° C.

10. A process as claimed in claim 1, wherein the aglycon is a monohydric aliphatic alcohol having 1 to 10 carbon atoms, a monohydric cycloaliphatic alcohol having from 5 to 7 carbon atoms or a saccharide.

11. A process as claimed in claim 10, wherein the aglycon is a monosaccharide.

12. A process for the manufacture of glycosides which comprises reacting a protected hexopyranosyl fluoride with a silyl ether of an aglycon in the presence of a metal fluoride of group IV or V of the periodic table, said metal having an atomic number of at least 22 and being present in the fluoride in a higher, stable and non-oxidizing or weakly oxidizing stage.

13. A process as claimed in claim 12, wherein the reaction is carried out with the trimethylsilylether of an aglycon.

14. A process for the manufacture of glycosides which comprises reacting a protected hexopyranosyl fluoride with an aglycon in a heterogenic phase in the presence of a metal fluoride of group IV of the periodic table which is not or only scarcely soluble in the reaction system, said metal having an atomic number of at least 22 and being present in the fluoride in a higher, stable and non-oxidizing or weakly oxidizing stage.

15. A process as claimed in claim 14, wherein the fluoride is applied in an amount of from 1 to 200 mole-% with respect to the hexopyranosyl fluoride.

16. A process as claimed in claim 14, wherein the reaction is carried out in the presence of a solvent for saccharides or of an inert medium.

17. A process as claimed in claim 14, wherein the reaction is carried out at a temperature in the range from −40° C. to +60° C.

18. A process as claimed in claim 14, wherein the aglycon is selected from the group consisting of monohydric aliphatic alcohols having 1 to 10 carbon atoms, monohydric cycloaliphatic alcohols having from 5 to 7 carbon atoms and saccharides.

19. A process as claimed in claim 14, wherein the aglycon is a monosaccharide.

20. A process as claimed in claim 14, wherein the metal fluoride is titanium tetrafluoride.

* * * * *